United States Patent [19]

Millard et al.

[11] Patent Number: 5,076,288
[45] Date of Patent: Dec. 31, 1991

[54] DOUBLE-LOCK FRICTION FASTENER SYSTEM

[75] Inventors: John Millard, Dana Point; John T. Posey, Altadena, both of Calif.

[73] Assignee: J. T. Posey Company, Arcadia, Calif.

[21] Appl. No.: 483,953

[22] Filed: Feb. 9, 1990

Related U.S. Application Data

[63] Continuation of Ser. No. 339,152, Apr. 17, 1989, abandoned.

[51] Int. Cl.$^5$ .............................................. A61F 13/00
[52] U.S. Cl. ...................................... 128/869; 24/493; 128/878; 128/DIG. 15
[58] Field of Search .............................. 128/869–870, 128/871, 873, 874, 875, 876, 878, 879, 888, DIG. 15; 24/442, 306; 2/DIG. 6

[56] References Cited

U.S. PATENT DOCUMENTS

| | | | |
|---|---|---|---|
| 3,297,026 | 1/1967 | Van Pelt | 128/878 |
| 3,376,865 | 4/1968 | Gamper | 128/169 |
| 3,474,781 | 10/1969 | Gaylord, Jr. | 128/876 |
| 3,503,101 | 3/1970 | Kolozsvary | 24/443 |
| 3,535,718 | 10/1970 | Murcott | 128/878 |
| 3,788,309 | 1/1974 | Zeilman | 128/874 |
| 4,414,969 | 11/1983 | Heyman | 128/878 |
| 4,422,455 | 12/1983 | Olsen | 128/878 |
| 4,832,053 | 5/1989 | McCarthy | 128/869 |

Primary Examiner—Robert A. Hafer
Assistant Examiner—Sam Rimell
Attorney, Agent, or Firm—Christie, Parker & Hale

[57] ABSTRACT

A double-lock friction fastener system useful as a restraint for hospital patients includes separate flexible first and second straps affixed to one another at a juncture and extending adjacent one another in the same general direction so that cooperating friction fasteners on free end portions of the straps can be frictionally secured to form a loop of infinitely adjustable size for attachment to an extremity of a patient to be restrained. A locking strap affixed to one strap is folded over the outer face of the other strap, and cooperating friction fasteners on the inside face of the locking strap and on the outer face of the other strap are frictionally secured so the folded-over locking strap covers the free end of the other strap and forms a double-lock friction fastener which resists pulling apart of the friction fasteners which form the loop. The double-lock friction fastener loops can be at opposite ends of a main strap, with one loop affixed to a patient and the other loop fastened to a remote fixture, such as a gurney or operating table. The double-lock friction fastener also can be used in a secure fastener system for closures for garments, or to fasten other objects to a fixture or the like.

4 Claims, 8 Drawing Sheets

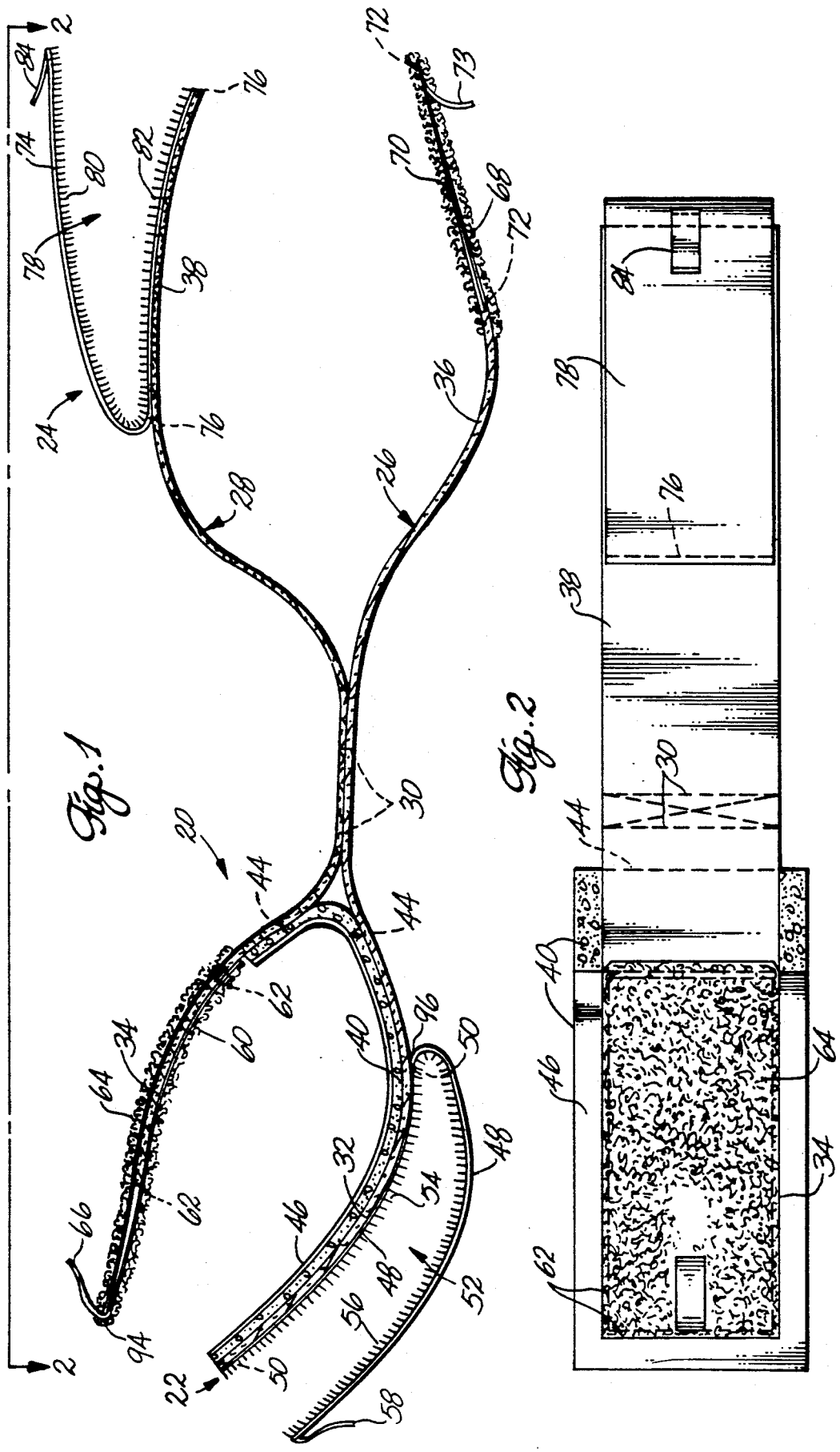

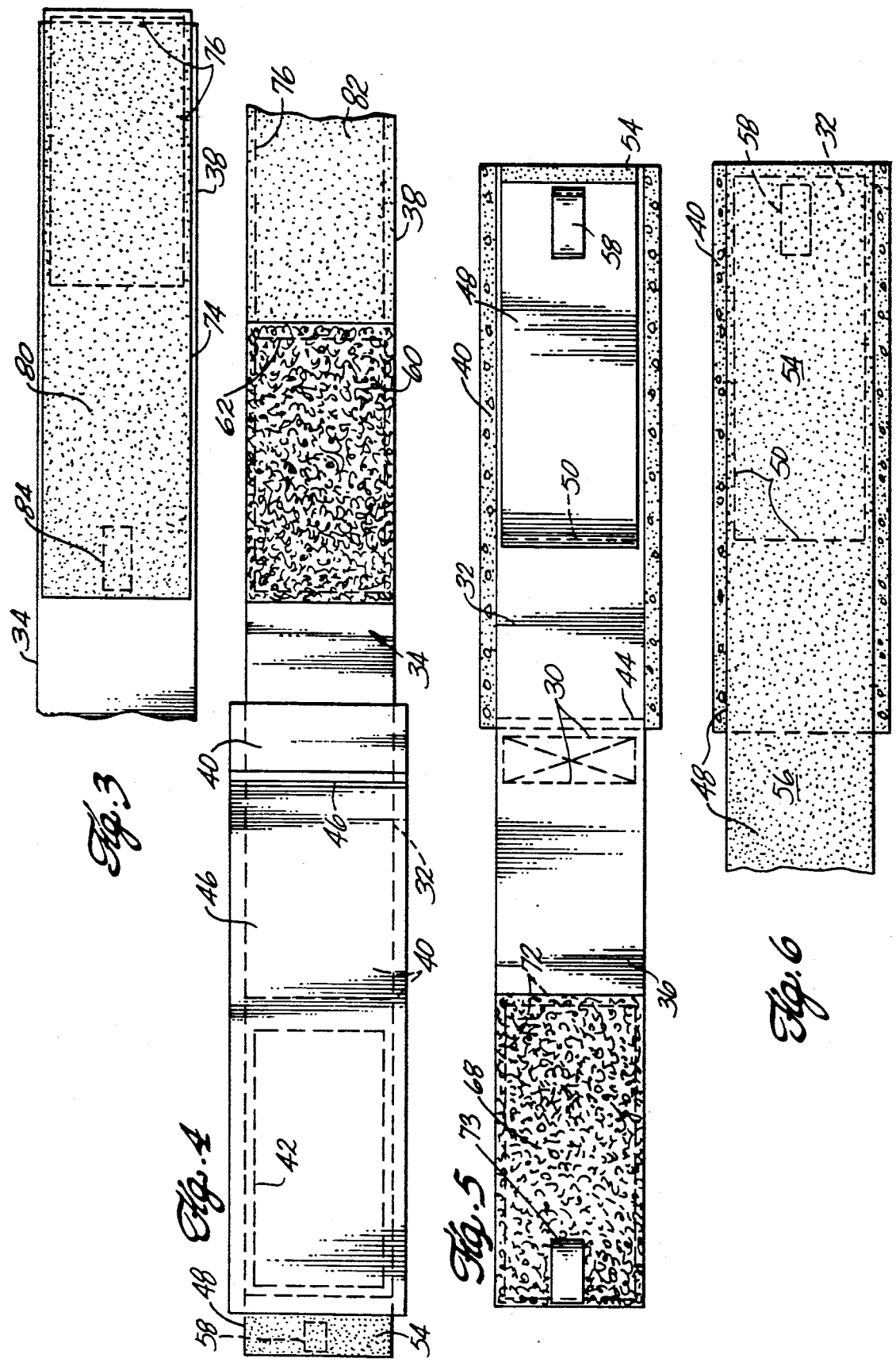

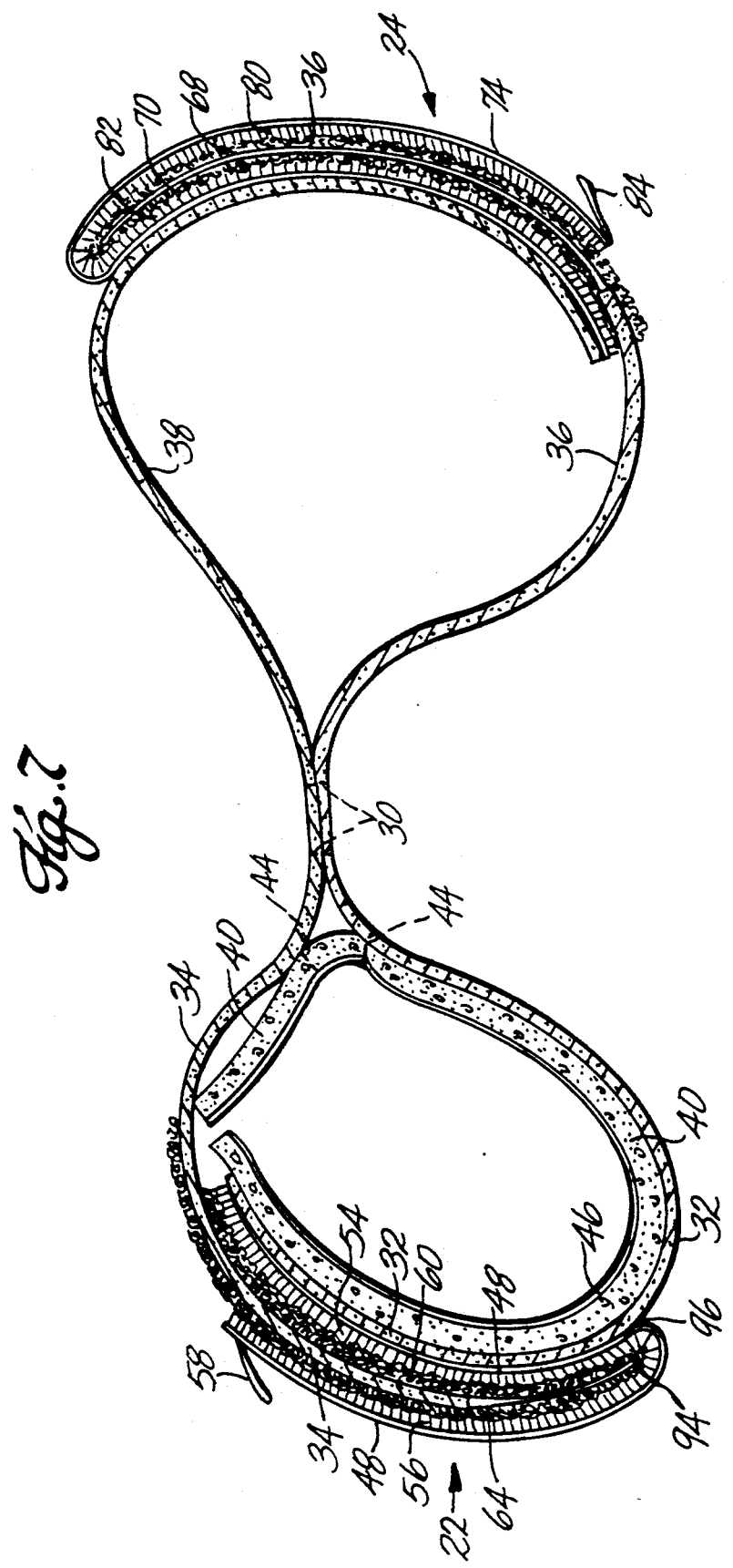

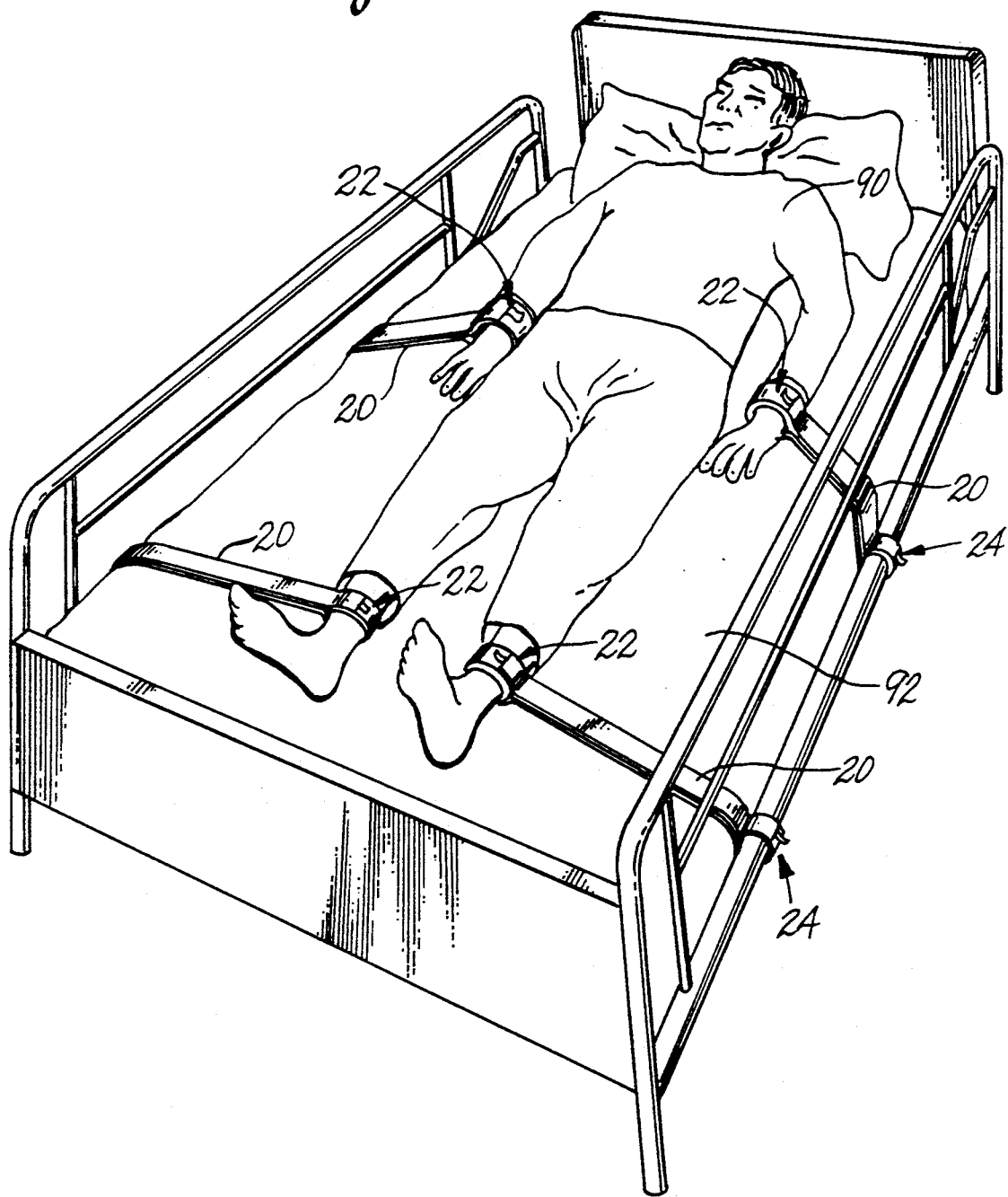

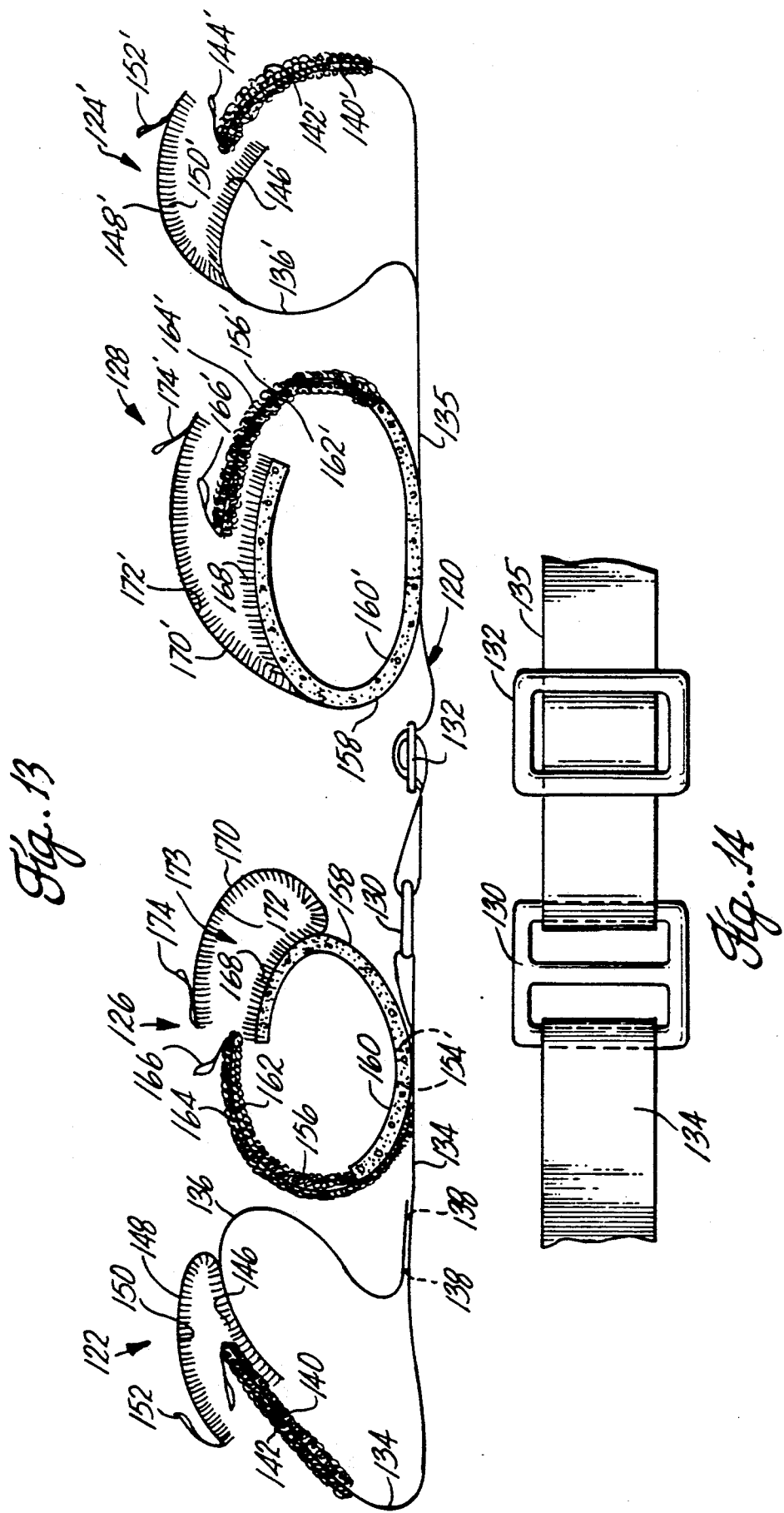

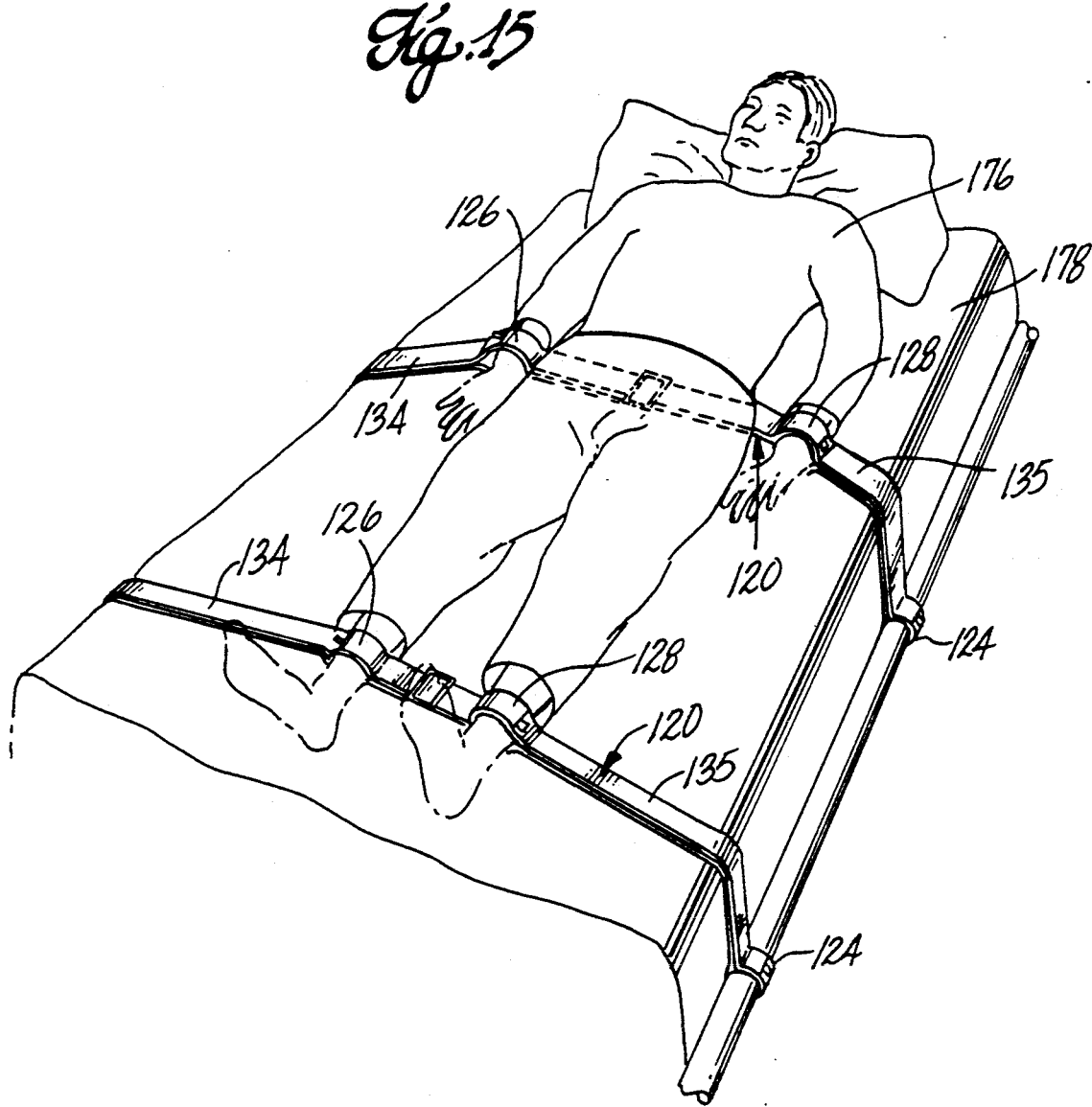

DOUBLE-LOCK FRICTION FASTENER SYSTEM

CROSS-REFERENCE TO RELATED APPLICATIONS

This is a continuation of application Ser. No. 07/339,152, filed 04/17/89, now abandoned.

FIELD OF THE INVENTION

This invention relates to restraining devices, and more particularly to a double-lock friction fastener system especially useful in hospital patient restraints, although the invention has other uses.

BACKGROUND OF THE INVENTION

Various hospital patient restraints and safety aids have been used in the past for securing hospital patients in beds or wheelchairs and on gurneys, stretchers or operating tables. These devices are reasonably satisfactory for keeping the patient restrained, but they are not particularly comfortable because they often must be fastened tightly to prevent unnecessary movement or to prevent the patient from freeing himself. Many previously used restraining devices are bulky or heavy and are therefore uncomfortable for the patient. Comfort is an important consideration because hospital patients who are reasonably comfortable when the restraint device is in use tend to be more cooperative.

Previous hospital patient restraints have included leather straps or belts fastened to the patient's extremities, such as the ankles or wrists, for restraining the patient in a hospital bed, or on a gurney or an operating table. These devices were especially uncomfortable and often required too much time to fasten or release in an emergency situation. The leather restraint devices were later replaced generally by limb holders or cuffs with Velcro-type hook-and-loop closures fastened to the patient's wrists or ankles. These devices give a more comfortable fit with the necessary assurance to the patient. They are also releasable from the patient immediately. In addition, they are machine washable and reasonably inexpensive for the hospital or nursing home.

In some hospital situations, patients must be restrained with complete security. These instances occur with patients who may be disturbed or are constantly thrashing about, or possibly patients who have drug problems. If these patients are restrained by a limb holder fastened by a conventional hook-and-loop fastener, the patient may be able to pull on the restraining device with enough force to pull apart the hook-and-loop fastener; and in some instances, the patient can make it difficult for the hospital attendant to immediately fasten the restraint in a secure fashion.

Other hospital restraints have included sleeved restraining vests which are used for restraining hospital patients in wheelchairs. These vests are typically closed at the back by a zipper running from the top to the bottom of the vest. There have been instances in which vests attached by a zipper have not kept a patient from pulling apart the back of the vest. Another disadvantage of a restraining vest fastened by a zipper is that it interferes with X-raying of the patient wearing the vest.

The present invention provides a friction fastener system which can be used with various hospital restraints and safety aids to restrain a patient with reasonable comfort while providing a secure restraint. The restraint system also can be fastened or released immediately to or from its secure position on the patient, it is relatively inexpensive to manufacture, and it is machine washable. The invention is especially useful in providing a reasonably comfortable yet secure restraint for hospital patients who are uncooperative.

SUMMARY OF THE INVENTION

Briefly, one embodiment of this invention provides a double-lock friction fastener system useful in a restraint for hospital patients. The restraint system includes separate elongated flexible first and second fastener portions extending adjacent to one another so that cooperating friction fasteners on the fastener portions facing one another can be frictionally secured to form a closure. An elongated flexible locking strap affixed to one of the fastener portions is folded over the outer face of the other fastener portion, and cooperating friction fasteners on the inside face of the locking strap and on the outer face of the other fastener portion are frictionally secured, so that the folded-over locking strap covers the free end of the other fastener portion. This forms a double-lock friction fastener which resists pulling apart of the friction fastener used for securing the first and second fastener portions.

The invention can be used for forming a double-lock friction fastener loop between adjacent first and second straps forming a patient limb holder, for example. The double-lock friction fastener loop can be at one end of an elongated main strap, having at its opposite end a similar double-lock friction fastener loop for attachment to a remote fixture such a gurney or hospital bed.

In another form of the invention, the double-lock friction fastener system can be in the form of an elongated main strap adapted for attachment to a hospital gurney or bed, together with a pair of spaced apart double-lock friction fastener loops affixed to the main strap which is adjustable in length between the two double-lock loops. This invention provides a means for securely holding a hospital patient in a bed, on a gurney, or an operating table, without any possible movement of the arms or legs.

The double-lock closure also is adaptable for forming a secure closure for hospital patient restraining vests and the like.

These and other aspects of the invention will be more fully understood by referring to the following detailed description and the accompanying drawings.

DRAWINGS

FIG. 1 is a semi-schematic end elevation view illustrating a restraining device according to principles of this invention in an open or unfastened position.

FIG. 2 is a front elevation view taken on line 2-2 of FIG. 1 and illustrating one side of the restraining device shown in FIG. 1.

FIG. 3 is a fragmentary elevation view similar to FIG. 2 illustrating a right hand portion of the restraining device unfolded from the position shown in FIG. 2.

FIG. 4 is a fragmentary elevation view of the restraining device inverted from the position shown in FIG. 2.

FIG. 5 is a side elevation view reversed from the position shown in FIG. 4 for showing an opposite side of the device, and in which a portion of the left side of the restraining device is folded over from the position shown in FIG. 4.

FIG. 6 is a fragmentary side elevation view similar to FIG. 5 but showing a portion of the right side of the restraining device unfolded from the position shown in FIG. 5.

FIG. 7 is a semi-schematic end elevation view illustrating use of the restraining device of FIG. 1 for forming a pair of friction loop fasteners.

FIG. 8 is a semi-schematic perspective view illustrating the restraining device of FIGS. 1-7 in use on a hospital patient.

FIG. 13 is a semi-schematic end elevation view illustrating an alternative form of the invention comprising multiple double-lock friction loop fasteners affixed to an adjustable restraining device.

FIG. 14 is a fragmentary elevation view illustrating a means of adjusting the length between a pair of friction fastener loops in the restraining device shown in FIG. 13.

FIG. 15 is a semi-schematic perspective view illustrating use of the restraining device of FIGS. 13 and 14 on a hospital patient.

DETAILED DESCRIPTION

Figure 9:
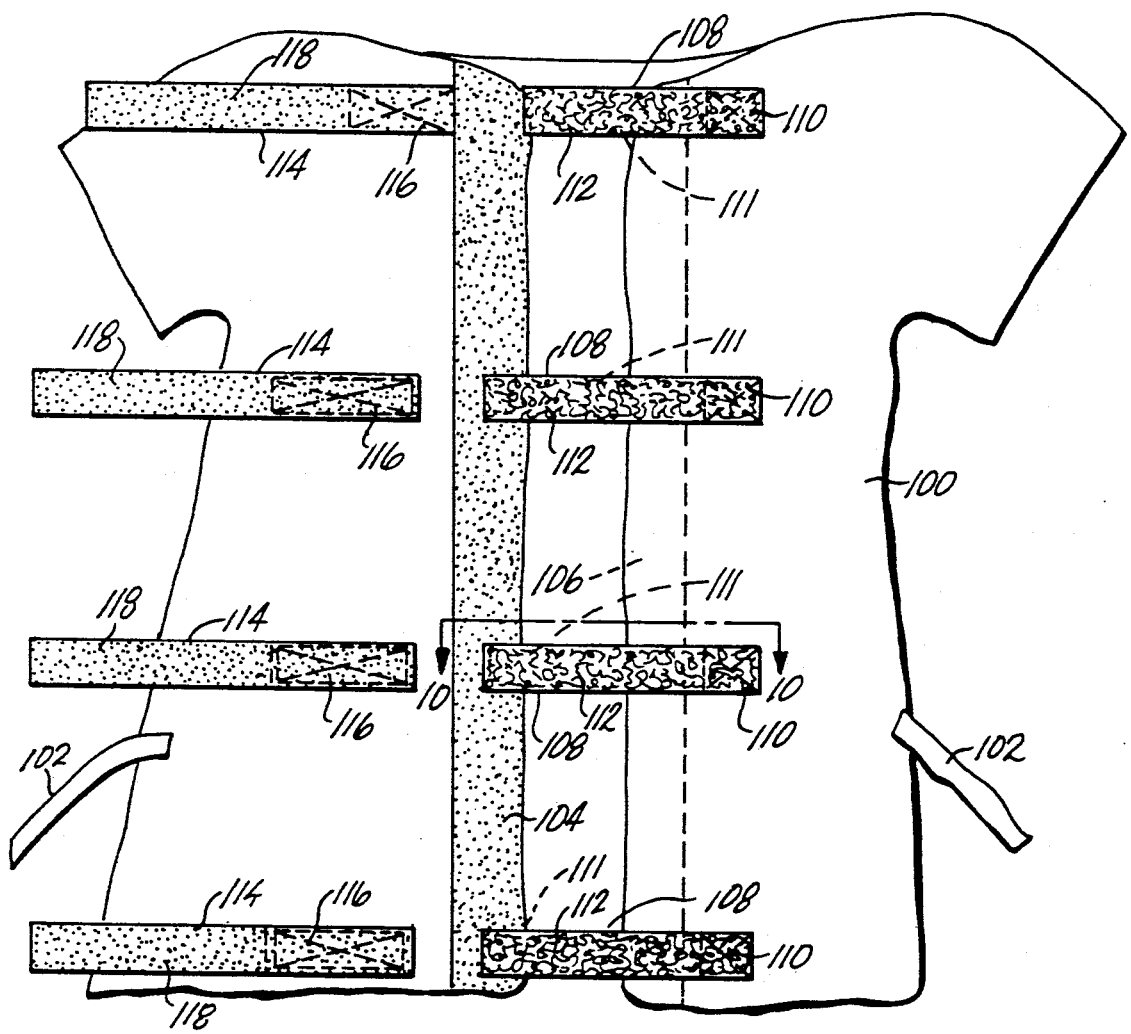
FIG. 9 is a side elevation view showing the back side of a restraining vest having a rear closure formed by a double-lock friction fastener system according to principles of this invention.
Figure 10:
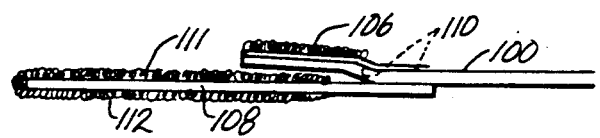
FIG. 10 is an end elevation view taken on line 10—10 of FIG. 9.

FIGS. 1 though 7 illustrate one embodiment of the present invention which comprises a double-security restraint device in the form of a limb holder 20 having a system of loop-forming straps 22 at the left end of the device, and a similar system of loop-forming straps 24 at the right end of the restraining device. The limb holder includes an elongated flexible first main strap 26 and an elongated flexible second main strap 28. The two straps are positioned adjacent to one another and are of approximately the same length and are offset from one another longitudinally and are then rigidly secured to each other by stitching 30 which defines a juncture. In the illustrated embodiment, the two main straps are secured to each other at about the middle of the two adjacent straps, although this location can vary. The two main straps are preferably each made from a strong webbing similar to seat belt material. A preferred material is woven nylon.

The first and second main straps extend to the left of the juncture at 30 to provide a long flexible left strap 32 adjacent to a somewhat shorter flexible left strap 34, respectively; and similarly, the first and second main straps extend to the right of the juncture at 30 to provide an elongated and flexible right strap 36 adjacent to a somewhat longer flexible right strap 38.

The loop-forming fasteners 22 on the left side of the restraint form an adjustable fastener to be secured around a patient's arm or wrist. The loop-forming fasteners 24 on the right side of the restraint form a fastener that can be anchored to a fixture such as a gurney or hospital bed, for example.

The loop-forming fasteners 22 on the left side of the restraint provide resilient padding in the form of an elongated elastomeric or plastic foam pad 40. The padding is generally U-shaped in configuration and is affixed to the inside face of the fastener strap 32 along the entire length of this strap. The padding extends in a U around the juncture between the two straps and then a short length of the padding overlies the inside face of the fastener strap 34 a short distance past the juncture. The padding 40 is fastened to the inside face of the strap 32 by a rectangular row of stitching 42 (see FIG. 4) and two rows of stitching 44 on opposite sides of the juncture between the straps 32 and 34. The padding is preferably made from a reasonably dense elastomeric material, such as a closed cell neoprene rubber. Preferably, the padding has a facing 46 of a soft woven fabric adhered to the exposed face of the padding.

An elongated flexible locking strap 48 is affixed to the outside face of the strap 32. The locking strap overlies the outer surface of the strap 32, and approximately one-half of the length of the locking strap is affixed to the strap 32 by a rectangular row of stitching 50. The other half of the locking strap is freely movable relative to the strap 32. FIG. 1 shows the freely movable free end portion of the locking strap 48 folded back to lie adjacent to and generally parallel to the strap 32, forming a gap 52 between the locking strap and the strap 32. FIG. 5 shows the locking strap 48 in its folded-over position, with the rectangular stitching 50 hidden by the free end portion of the locking strap.

The locking strap 48 is preferably made from an elongated piece of a rugged, flexible and inelastic material such as woven nylon. The entire length of the locking strap which faces the gap 52 has a hook-and-loop friction fastener material on it, such as the friction fastener commonly sold under the trademark Velcro. In the illustrated embodiment, the friction fastener on the locking strap is a Velcro hook-type fastener extending along the outer face of the strap 32 for approximately one-half its length, and a Velcro-type hook fastener material 56 extends along the inside face of the flexible free end portion of the locking strap 48. A flexible pull tab 58 is affixed to the outer face of the free end of the locking strap 48.

An elongated section of a Velcro-type loop fastener 60 is affixed to the inside face of the free end portion of the strap 34. The loop fastener 60 is adapted for fastening to the friction fastener 54 on the outer face of the strap 32 for forming an infinitely adjustable friction fastener loop at the left side of the restraint device. The loop fastener 60 is affixed to the strap 34 by a rectangular row of stitching 62, and the loop fastener 60 extends along the entire inside face of the strap 34 which extends away from the padding near the juncture of the two main straps. The loop fastener 60 on the inside face of the strap 34 is shown best in FIG. 4 in a position folded away from the strap 32.

An elongated section of a Velcro-type loop fastener 64 is affixed to the outer face of the strap 34. The stitching 52 fastens this loop fastener to the strap as well as the loop fastener 60. The loop fastener 64 is preferably of the same length as the loop fastener 60 and both loop fasteners extend inwardly from the free end of the strap 34 for approximately three-fourths of its length. The loop fastener 64 on the outer face of the strap 34 is adapted for fastening to the hook type friction fastener 56 on the free end portion of the locking strap 48. A flexible pull tab 66 is affixed to the outside face of the free end of the strap 34.

The double-lock loop fastener 24 on the right side of the restraint device is similar in construction to that described for the double-lock loop fastener 22. Briefly, the double-lock loop fastener 24 includes a Velcro-type loop fastener section 68 extending along the outside face of the strap 36 inboard from the free end of the strap. A similar Velcro-type loop fastener section 70 extends along the inside face of the strap 36 inboard from the free end of the strap. The two loop friction fasteners 68 and 70 are of approximately the same length, extending for about one-half the length of the strap 36, and both are affixed to the opposite faces of the strap by a rectangular row of stitching 72. A pull tab 73 is affixed to the outer face of the free end of the strap 36.

A locking strap 74 is affixed to the outer face of the free end portion of the strap 38. Approximately one-half of the locking strap is rigidly affixed to the strap 38 by a rectangular row of stitching 76. The remaining flexible free end portion of the locking strap 74 can be folded back, as illustrated in FIG. 1, to form a gap 78 between the inside of the locking strap 74 and the outer face of the strap 38. An elongated section of a Velcro-type hook material covers the inside face of the locking strap 74 along its free end portion and along the portion of the locking strap affixed to the outer face of the strap 38. This forms a hook-type friction fastener 80 on the inside of the locking strap and a hook-type friction fastener 82 on the outside face and free end portion of the strap 38. A flexible pull tab 84 is affixed to the outer face of the free end portion of the locking strap 74.

FIGS. 7 and 8 illustrate use of the restraining device 20 for securing a hospital patient 90 in a hospital bed 92. A pair of separate restraining devices are fastened around the wrists of the patient, and another pair of separate restraining devices are fastened around the ankles of the patient. The padded portions (the fastener 22 on the left side of the restraining device still illustrated in FIG. 1) is fastened to the patient's wrist or ankle, and the other end of each restraining device is then fastened to a fixed point on the hospital bed remote from the patient.

As shown best in FIG. 7, the padded inside portions of the fastener straps 32 and 34 are wrapped in a loop tightly around the wrist or ankle. The cooperating hook-and-loop friction fasteners 48 and 60 on the outer face of the strap 32 and the inner face of the strap 34, respectively, are fastened to each other to form a loop fastened around the patient's wrist or ankle. These cooperating friction fasteners provide an infinitely adjustable but releasable means of attaching the loop tightly around the patient. This leaves the free end 94 of the strap 34 adjacent the juncture 96 between the strap 32 and the fixed end of the free portion of the locking strap 48. In a conventional friction loop fastener, the patient may be able to pull on the fastener with sufficient force to pull apart the cooperating friction fasteners on the overlying straps which form the loop. The present invention avoids this problem by providing a double-security friction fastener system in which the free end portion of the locking strap 48 is folded back over the outer face of the outermost strap 34, with the cooperating hook-and-loop fasteners 56 and 64 on the inside face of the locking strap and the outer face of the strap 34 being frictionally secured to one another in a double-lock. That is, the attached locking strap extends over the free end portion 94 of the strap 34 which forms the outer portion of the friction loop fastener secured to the ankle or wrist The attached locking strap not only extends over the free end portion 94 of the strap 34 but also along a substantial portion of the outer surface of the strap 34. This provides a means of preventing separation between the underlying cooperating friction fasteners along the strap 34 and the strap 32. Thus, a double-security friction loop fastener is formed around the wrist or ankle of the patient.

The opposite end of the restraint shown in FIGS. 7 and 8 is affixed in a similar manner to the fixed point on the hospital bed. As shown on the right side of FIG. 7, the friction loop fastener 24 affixed to the hospital bed is formed by wrapping the fastener straps 36 and 38 around a fixture to form a loop with the cooperating hook-and-loop friction fasteners 70 and 82 on the end portions of the straps 36 and 38, respectively. The free end portion of the locking strap 74 is then folded back over the outside of the friction fasteners which are attached to form the loop, and the cooperating hook-and-loop fasteners 68 and 80 on the outer face of the strap 36 and on the inside face of the locking strap 74 are fastened to one another along the overlapping fastened portions of the straps 36 and 38. Thus, in a similar manner, the locking strap 74 forms a doublesecurity fastener which prevents the friction fasteners 70 and 82 from being pulled apart by forces applied to the restraint during use.

In an emergency situation, for example, the friction fastener loops 22 and 24 can be easily removed from the patient or fixture. To release the friction fastener loop 82 from the patient, the locking strap 48 is quickly pulled away from its frictional attachment using the pull tab 58, thereby exposing the free end 94 of the strap 34 and its pull tab 66. The strap 34 is then pulled away from its attachment to the strap 32 using the pull tab 66, resulting in a quick release of the friction loop fastener. The friction loop fastener 24 at the other end of the restraint device is quickly removed in a similar manner.

The invention described in FIGS. 1 through 7 is one example of several embodiments of restraint devices using the double-security friction loop fastener system. In other embodiments, a double-lock friction loop fastener may be affixed to one end of an elongated strap and the other end of the strap can have no added fastening means but can simply be used by itself for tying to a fixture. Alternatively, the remote end of the strap can also include fasteners for securing the strap to a fixture in place of the friction loop fastener 24. Further, the distance between the friction loop fasteners 22 and 24 at the opposite ends of an elongated strap can vary, depending upon the distance between the patient and the fixture to which the other end of the restraint device is attached. In addition, the locking straps 48 and 74 are shown in FIG. 1 on opposite sides of the restraint device. However, in other embodiments the combination of the hook-and-loop fastener sections on the different faces of the straps can be modified, with the locking straps both being on the same side of the restraint device, if desired.

FIGS. 9 through 12 illustrate an alternate form of the invention in which a double-security friction fastener system is used to form a closure along the back side of a restraining vest 100 worn by a hospital patient. This restraining device can be similar to the restraining device disclosed in U.S. Pat. No. 4,685,454 of J. T. Posey Company, the assignee of this application. The restraining vest 100 includes ties 102 at the sides of the vest, together with other means for restraining the patient which are described in U.S. Pat. No. 4,685,454 incorporated herein by this reference. The patent discloses use of a zipper along the back of the vest for closing the vest behind the patient. The zipper must be offset from the rear center of the jacket so that it does not apply pressure to the spinal column of the patient when the jacket is worn. However, use of the zipper at the back of the restraining device can be a disadvantage, particularly on uncooperative patients who can reach behind themselves and pull apart the back of the restraining device along either or both sides of the zipper. Use of the zipper also prevents X-raying of the patient.

The embodiment illustrated in FIGS. 9 through 12 comprises an alternative means of fastening the restraining device 100 along the back of the vest by a double-security friction fastener system of this invention. This fastener system includes cooperating hook-and-loop fastener strips extending along the opposite edges of the rear opening to the vest. In the illustrated embodiment, an elongated flexible Velcro hook-type fastener 104 extends along an outer face of the vest at one edge of the rear opening, and an elongated flexible Velcro-type loop fastener 106 extends along an inside face of the vest at the other edge of the rear opening. These two cooperating friction fastener strips are overlaid and pressed together to frictionally secure the edges at the rear closure of the vest. The fastener system at the rear of the vest further includes a system of double-security frictional fastener straps which include vertically spaced apart and elongated fastener straps 108, each affixed to the outer face of the garment and extending across the edge of the opening closed by the Velcro loop fastener strip 106. The horizontally extending fastener straps are each affixed to the garment by stitching 110. The flexible free end portions of the straps each extend toward the other side of the opening. Strips of a Velcro-type loop material 111 and 112 are affixed to the opposite inside and outside faces of the free end portions of the straps 108, respectively. On the other side of the opening, a series of vertically spaced apart elongated flexible straps 114 are affixed to the garment adjacent the hook fastener strip 104. The straps 114 are each affixed to the garment by stitching 116 at the same elevations as the straps 108 on the opposite side of the rear opening. The free end portions of the flexible straps 114 normally extend away from the straps 108 on the opposite side of the rear opening, as shown best in FIG. 9. Separate strips of a Velcro-type hook material 118 are affixed to the outer faces of the straps 114. The straps 114 are preferably about twice as long as the free end portions of the straps 108.

Figure 11:
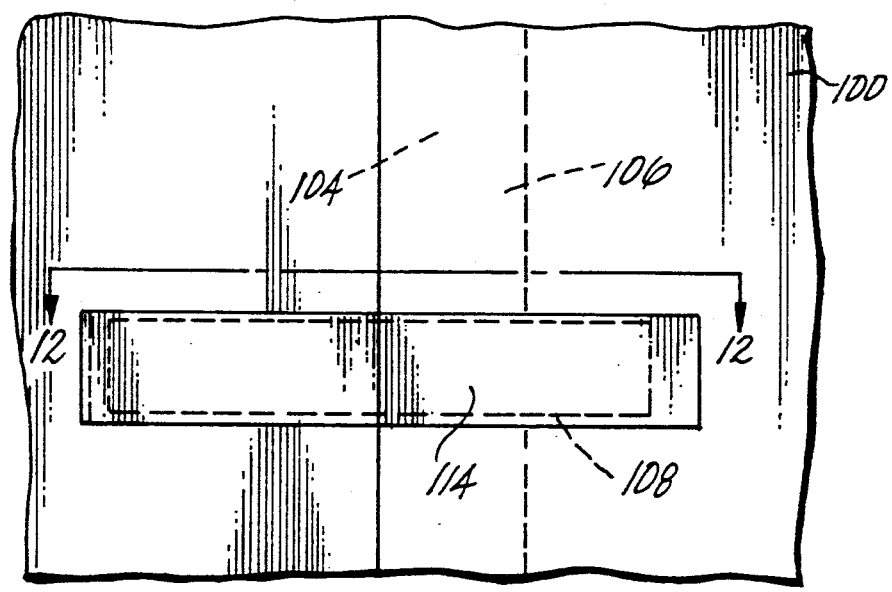
FIG. 11 is an enlarged fragmentary side elevation view illustrating the double-lock friction fasteners of FIG. 10 in their closed position.
Figure 12:
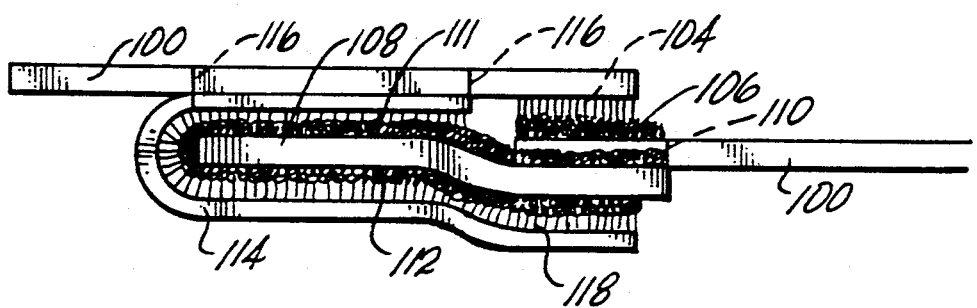
FIG. 12 is an end elevation view taken on line 12—12 of FIG. 11.

In using the double-security fastener system for the restraining vest, the cooperating vertically extending hook-and-loop fasteners 104 and 106 are first fastened to each other to close the opening along the back of the vest. This closure is then secured by the double-security fastener system provided by the cooperating pairs of fastener straps 108 and 114 The loop fasteners 111 on the inside faces of the straps 108 are fastened to the hook fasteners 118 on the outer faces of the straps 114. The fastener straps 108 overlie the fixed inside portions of the straps 114 closest to the opening in the vest. This leaves the outer free end portions of the straps 114 free to be folded back over the outer faces of the straps 108 to form a double-security lock. The double-lock is formed by fastening the hook fasteners 118 on the free end portions of the straps 114 to the loop fasteners 112 on the outer faces of the straps 108. The double-security lock is best shown in FIG. 12. FIG. 11 shows an elevation view of the double-security lock.

FIGS. 13 and 14 schematically illustrate a further embodiment of the invention which comprises a one-piece, multiple double-security friction loop fastener system. In this embodiment, left and right double-security friction loop fasteners 122 and 124 are affixed to the outer ends of an elongated adjustable strap. In addition, padded left and right double-security friction loop fasteners 126 and 128 are secured to intermediate portions of the strap on opposite sides of a pair of buckles 130 and 132 which provide a means for adjusting the length of the strap between the two intermediate loop fasteners 126 and 128. The two buckles are conventional in their means of adjusting the length of the strap, by which the buckle 132 is slid toward or away from the buckle 130 to adjust the overall length of the strap.

The double-security friction loop fastener system 122 includes a flexible strap 134 formed by the end of the main strap, and a second flexible elongated strap 136 rigidly affixed by stitching 138 to the strap 134. The free end portion of the strap 134 has elongated sections of a Velcro-type loop fastener 140 on its inside face and a loop fastener 142 on its outside face. A pull tab 144 is at the free end of the strap 134. An elongated section of a Velcro-type hook fastener 146 extends along the outside face at the free end of the strap 136 to face toward the loop fastener 140. A flexible locking strap 148 affixed to the outer face of the strap 136 has an elongated section of a Velcro-type hoop material 150 on its inside face for facing toward the friction loop fastener 142 on the strap 134. A flexible pull tab 152 is affixed to the free end of the locking strap 148. The friction fastener system 122 is used in a manner described previously by fastening the overlying free ends of the straps 134 and 136 to form a loop of adjustable size and then folding back the locking strap 148 over the free end of the strap 134 and fastening the locking strap 148 to the outer face of the strap 134.

The double-security friction loop fastener system 124 at the opposite end of the strap 135 is similar in structure and function to the friction fastener system 122.

The double-security friction fastener loop 126 includes an elongated flexible main strap affixed at about its mid-point to the strap 134 by stitching 154. This leaves free end portions of the fastener strap extending away from the main strap to form first and second straps 156 and 158 on the left and right sides of the loop fastener 126. Padding 160 is affixed to the inside faces of the straps 156 and 158. A Velcro-type loop fastener material 162 extends along the free end portion of the inside face of the strap 156. A Velcro-type loop fastener material 164 also extends along the outside face of the strap 156 for most of its length. A flexible pull tab 166 is secured to the outer face at the free end of the strap 156. An elongated section of a Velcro-type hook material 168 extends along the outer face of the free end portion of the strap 158. An elongated flexible locking strap 170 is secured to the outer face of the strap 158 at a juncture spaced inwardly from the free end of the strap 158. A Velcro-type hook material covers the inside face of the locking strap 170 for facing toward the hook fastener 168 on the outer face of the strap 158. This leaves a gap 173 between the inside of the locking strap and the outside of the strap 158. The double-security friction loop 126 is used in a manner described previously by wrapping the padded portion around the patient's wrist or ankle, fastening the hook and loop fasteners 162 and 168 to form a fastener loop of adjustable size, and then folding the locking strap back over the outside face of the strap 156 and fastening the hook and loop fasteners 172 and 164 to provide the double-security lock.

The double-security friction loop fastener 128 has a similar structure and function to the friction loop fastener 126 previously described.

FIG. 15 illustrates use of the multiple double security restraining device shown in FIGS. 13 and 14. In this embodiment, a patient 176 is restrained in a hospital bed 178 by a pair of the restraining devices, one extending across the bed at wrist level and one extending across the bed at ankle level. The length of the each strap 120 is adjusted by the slide buckle 132 so that the strap portions 134 and 135 lie flat against the upper surface of the bed. The friction loop fasteners 122 and 124 are then rigidly fastened to fixed points at the sides of the bed so that the main strap 120 lies flat against the bed without any slack. The friction loop fasteners 126 and 128 are then fastened to the ankles and wrists of the patient to provide double security fasteners for securing the wrists and ankles of the patient to the main straps 120. Since the friction loop fasteners attached to the patient's extremities are in turn affixed to the main strap 20 without any relative freedom of motion, the patient's wrists and ankles are firmly affixed to the bed without any possibility of movement relative to the bed.

What is claimed is:

1. A hospital patient restraining device having an elongated flexible restraining strap including means at one end thereof for releasable attachment to a fixture remote from the patient and having a friction loop fastener system affixed to an opposite end thereof for placement around a bodily limb of a patient, the friction loop fastener system comprising:

an elongated flexible first strap and a separate elongated flexible second strap, both affixed to the restraining strap and extending freely and independently adjacent to one another in the same general direction away from the restraining strap, the first strap having an inner face and an outer face adjacent a free end thereof, the second strap having an outer face adjacent a free end thereof, an elongated first friction fastener affixed to the inner face of the first strap, an elongated second friction fastener affixed to the outer face of the first strap, and an elongated third friction fastener affixed to the outer face of the second strap, an elongated flexible locking strap affixed to and extending freely and independently adjacent to the outer face of the second strap and having an inner face for extending adjacent to the third friction fastener on the outer face of the second strap, and an elongated fourth fiction fastener affixed to the inner face of the locking strap, the first and second flexible straps each having a sufficient length so that the first and second straps are formed as a loop at one end of the restraining strap to wrap around the bodily limb of the patient, with the inner face of the first strap and the outer face of the second strap overlying one another along substantial lengths thereof, with the first and third friction fasteners being frictionally secured to each other for forming an infinitely adjustable and releasable friction loop fastener round the limb of the patient, the second friction fastener facing away from the friction loop fastener, the inner face of the locking strap having a sufficient length for overlying the outer face of the fastened first strap with the second and fourth friction fasteners being frictionally secured to each other so the locking strap fastened to the outer face of the first strap forms a releasable, frictional double-lock for the friction loop fastener.

2. The article according to claim 1 including a flexible pull tab at the free end of the first strap on the second friction fastener and a flexible pull tap adjacent the free end of the locking strap on the outer face thereof.

3. The article according to claim 1 including padding on the inside face of the second strap and on a portion of the inside face of the first strap extending away from a juncture between the first and second straps.

4. The article according to claim 1 in which the first and second straps extend away from a first juncture at the end of the restraining strap, and the locking strap extends away from a second juncture on the second strap spaced from the first juncture.

* * * * *

UNITED STATES PATENT AND TRADEMARK OFFICE
CERTIFICATE OF CORRECTION

PATENT NO. : 5,076,288
DATED : December 31, 1991
INVENTOR(S) : John Millard; John T. Posey It is certified that error appears in the above-identified patent and that said Letters Patent is hereby corrected as shown below:

Column 2, line 32, after "such" insert -- as --.

Column 5, line 66, after "wrist" insert a period.

Column 6, line 21, change "doublesecurity" to
 -- double-security --.

Column 7, line 42, change "elevations" to -- elevation --.
Column 7, line 56, after "114" insert a period.

Column 9, line 3, change "!28" to -- 128 --.
Column 9, line 11, after "length of" delete "the".

Column 10, line 9, change "fiction" to -- friction --.
Column 10, line 20, change "round" to -- around --.

Signed and Sealed this

Twenty-fifth Day of May, 1993

Attest:

MICHAEL K. KIRK

*Attesting Officer*   Acting Commissioner of Patents and Trademarks